(12) United States Patent
Puls et al.

(10) Patent No.: US 9,968,545 B2
(45) Date of Patent: May 15, 2018

(54) AGENT FOR TEMPORARILY RESHAPING KERATIN-CONTAINING FIBERS COMPRISING PRESERVATIVE

(71) Applicant: Henkel AG & Co. KGaA, Duesseldorf (DE)

(72) Inventors: Anna Puls, Winsen (DE); Sandra Fuchs, Pinneberg (DE); Marcus Noll, Norderstedt (DE); Arne Junge, Hamburg (DE); Nora Koopmann, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days. days.

(21) Appl. No.: 15/377,245

(22) Filed: Dec. 13, 2016

(65) Prior Publication Data

US 2017/0172907 A1  Jun. 22, 2017

(30) Foreign Application Priority Data

Dec. 17, 2015  (DE) .................. 10 2015 225 557

(51) Int. Cl.
| | | |
|---|---|---|
| *A61K 8/92* | (2006.01) | |
| *A61K 8/31* | (2006.01) | |
| *A61K 8/36* | (2006.01) | |
| *A61K 8/73* | (2006.01) | |
| *A61Q 5/06* | (2006.01) | |

(52) U.S. Cl.
CPC .............. *A61K 8/927* (2013.01); *A61K 8/31* (2013.01); *A61K 8/36* (2013.01); *A61K 8/731* (2013.01); *A61K 8/922* (2013.01); *A61Q 5/06* (2013.01); *A61K 2800/524* (2013.01)

(58) Field of Classification Search
None
See application file for complete search history.

(56) References Cited

U.S. PATENT DOCUMENTS

2009/0071495 A1* 3/2009 Nguyen ................ A61K 8/361
132/203

FOREIGN PATENT DOCUMENTS

DE  19756454 C1  6/1999

OTHER PUBLICATIONS

Preliminary Amendment for U.S. Appl. No. 15/377,284, filed Dec. 13, 2016.
Substitute Specification for U.S. Appl. No. 15/377,284, filed Dec. 13, 2016.
Preliminary Amendment for U.S. Appl. No. 15/377,298, filed Dec. 13, 2016.
Substitute Specification for U.S. Appl. No. 15/377,298, filed Dec. 13, 2016.
Preliminary Amendment for U.S. Appl. No. 15/377,329, filed Dec. 13, 2016.
Substitute Specification for U.S. Appl. No. 15/377,329, filed Dec. 13, 2016.

* cited by examiner

*Primary Examiner* — Robert A Wax
*Assistant Examiner* — Quanglong N Truong
(74) *Attorney, Agent, or Firm* — Lorenz & Kopf LLP

(57) ABSTRACT

A shelf-stable cosmetic agent for temporarily shaping keratin fibers, and in particular human hair, having improved protection against phase separation and having increased microbiological stability is provided.

8 Claims, No Drawings

✂

AGENT FOR TEMPORARILY RESHAPING KERATIN-CONTAINING FIBERS COMPRISING PRESERVATIVE

CROSS-REFERENCE TO RELATED APPLICATION

This application claims priority to German Patent Application No. 10 2015 225 557.3, filed Dec. 17, 2015, which is incorporated herein by reference in its entirety.

TECHNICAL FIELD

The present disclosure relates to a cosmetic agent for temporarily shaping keratin fibers, and in particular human hair.

BACKGROUND

Temporarily creating hair styles for an extended period of up to several days generally requires the use of setting active ingredients. Hair treatment agents that are used to temporarily impart shape to the hair therefore play an important role. Corresponding agents for temporary reshaping usually comprise synthetic polymers and/or waxes serving as the setting active ingredient. Agents for supporting the temporary shaping of hair can be formulated in the form of hair spray, hair wax, hair gel, or hair foam, for example.

The most important property of an agent for temporarily reshaping hair, hereafter also referred to as a styling agent, is to give the treated fibers the strongest hold possible in the newly modeled shape, which is to say a shape that has been imparted to the hair. This is also referred to as strong styling hold or a high degree of hold of the styling agent. The styling hold is essentially determined by the nature and amount of the setting active ingredient that is used, although further components of the styling agent may also have an influence.

In addition to a high degree of hold, styling agents must satisfy a whole host of additional requirements. These can be broken down in approximate terms into properties of the hair, properties of the individual formulation, such as properties of the foam, of the gel, or of the sprayed aerosol, and properties that relate to the handling of the styling agent, wherein the properties of the hair are particularly important. In particular moisture resistance, low tack, and a balanced conditioning effect shall be mentioned. Moreover, a styling agent should be universally suitable for all hair types to an extent as great as possible, and be gentle on the hair and skin.

In order to meet the diverse requirements, a number of synthetic polymers have already been developed as setting active ingredients, which are used in styling agents. The polymers can be divided into cationic, anionic, non-ionic and amphoteric setting polymers. As an alternative or in addition, waxes are used as setting active ingredients. Ideally, the polymers and/or waxes form a polymer film when applied to the hair, or a film that gives the hair style a strong hold on the one hand, but on the other hand is sufficiently flexible so as not to break under stress.

Styling products that are present in the form of emulsions can moreover have instabilities in the form of synereses, which have the undesirable effect of resulting in a short shelf life.

BRIEF SUMMARY

Cosmetic agents for temporarily shaping keratin fibers and methods for temporarily shaping keratin fibers are provided. In accordance with an embodiment, a cosmetic agent for temporarily shaping keratin fibers comprises: (a) at least one wax having a melting point above about 37° C. in a total amount of about 1 to about 30 wt. %; (b) at least one emulsifier in a total amount of about 0.5 to about 20 wt. %; (c) at least one cellulose ether in a total amount of about 0.01 to about 3 wt. %; (d) propionic acid and/or salts of propionic acid in a total amount of about 0.01 to about 2 wt. %; and (e) water in a total amount of about 5 to about 90 wt. %, wherein the weight percent is based in each case on the total weight of the cosmetic agent.

In accordance with another embodiment, a method for temporarily shaping keratin fibers is provided. The method comprises providing a cosmetic agent comprising: (a) at least one wax having a melting point above about 37° C. in a total amount of about 1 to about 30 wt. %; (b) at least one emulsifier in a total amount of about 0.5 to about 20 wt. %; (c) at least one cellulose ether in a total amount of about 0.01 to about 3 wt. %; (d) propionic acid and/or salts of propionic acid in a total amount of about 0.01 to about 2 wt. %; and (e) water in a total amount of about 5 to about 90 wt. %, wherein the weight percent is based in each case on the total weight of the cosmetic agent. The method further comprises applying the cosmetic agent to the keratin fibers.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Shelf-stable, wax-containing cosmetic agents for temporarily shaping keratin fibers are provided herein.

In this regard, a cosmetic agent for temporarily shaping keratin fibers comprises:
(a) at least one wax having a melting point above about 37° C. in a total amount of about 1 to about 30 wt. %;
(b) at least one emulsifier in a total amount of about 0.5 to about 20 wt. %;
(c) at least one cellulose ether in a total amount of about 0.01 to about 3 wt. %;
(d) propionic acid and/or salt(s) of propionic acid in a total amount of about 0.01 to about 2 wt. %; and
(e) water in a total amount of about 5 to about 90 wt. %, wherein the weight information is based in each case on the total weight of the cosmetic agent.

Cosmetic agents for temporarily shaping human hair are also referred to as styling agents. The present disclosure relates in particular to styling agents such as hair waxes, pastes, lotions or clays. The product form "clay" refers to high viscosity, wax-like cosmetic agents containing clay compounds (such as kaolin), among other things.

Surprisingly, it was found within the scope contemplated herein that adding propionic acid and/or salt(s) of propionic acid to a cosmetic agent for temporarily reshaping keratin fibers, and in particular human hair, helped increase the physical stability of cosmetic agents in the form of emulsions, and that these agents exhibit no phase separation (syneresis).

Moreover, the microbiological stability of the cosmetic agents was increased.

Other properties that are usually required of cosmetic agents for temporarily shaping keratin fibers such as long-term hold, stiffness and low tack are preserved.

As contemplated herein, the term "keratin fibers" comprises furs, wool and feathers, but in particular human hair.

The cosmetic agent comprises at least one natural or synthetic wax having a melting point of above about 37° C. as component (a). The cosmetic agent comprises the at least one wax in a total amount of about 1 to about 30 wt. %, preferably about 2 to about 25 wt. %, and more preferably about 2.5 to about 20 wt. %, based on the total weight of the cosmetic agent.

Natural or synthetic waxes that can be used include solid paraffins or isoparaffins, plant-based waxes such as candelilla wax, carnauba wax, esparto grass wax, Japan wax, cork wax, sugar cane wax, ouricury wax, montan wax, sunflower wax, fruit waxes, and animal waxes, such as beeswaxes and other insect waxes, cetaceum, shellac wax, wool fat and rump fat, furthermore mineral waxes such as ceresin and ozokerite, or petrochemical waxes, such as petrolatum, paraffin waxes, microwaxes made of polyethylene or polypropylene, and polyethylene glycol waxes. It may be advantageous to use hydrogenated waxes. Furthermore, it is also possible to use chemically modified waxes, in particular the hard waxes, such as montan ester waxes, sasol waxes and hydrogenated jojoba waxes.

Also suitable are the triglycerides of saturated and optionally hydroxylated C16-30 fatty acids, such as hydrogenated triglyceride fats (hydrogenated palm oil, hydrogenated coconut oil, hydrogenated castor oil), glyceryl tribehenate or glyceryltri-12-hydroxy stearate, furthermore synthetic full esters of fatty acids and glycols (such as Syncrowachs®) or polyols having 2 to 6 carbon atoms, fatty acid monoalkanol amides including a C12-22 acyl group and a C2-4 alkanol group, esters of saturated and/or unsaturated, branched and/or unbranched alkane carboxylic acids having a chain length of 1 to 80 carbon atoms and saturated and/or unsaturated, branched and/or unbranched alcohols having a chain length of 1 to 80 carbon atoms, including, for example, synthetic fatty acid/fatty alcohol esters such as stearyl stearate or cetyl palmitate, esters of aromatic carboxylic acids, dicarboxylic acids or hydroxycarboxylic acids (such as 12-hydroxystearic acid), and saturated and/or unsaturated, branched and/or unbranched alcohols having a chain length of 1 to 80 carbon atoms, lactides of long-chain hydroxycarboxylic acids, and full esters of fatty alcohols and dicarboxylic and tricarboxylic acids, such as dicetyl succinate or dicetyl/distearyl adipate, and mixtures of these substances.

The wax components can also be selected from the group of the esters of saturated, unbranched alkane carboxylic acids having a chain length of 14 to 44 carbon atoms and saturated, unbranched alcohols having a chain length of 14 to 44 carbon atoms, provided the wax component or the collectivity of the wax components is solid at room temperature. The wax components can be selected, for example, from the group consisting of the C16-36 alkyl stearates, the C10-40 alkyl stearates, the C2-40 alkyl isostearates, the C20-40 dialkyl esters of dimer acids, the C18-38 alkyl hydroxystearoyl stearates, the C20-40 alkyl erucates, and furthermore C30-50 alkyl beeswax and cetearyl behenate can be used. Silicone waxes, such as stearyl trimethylsilane/stearyl alcohol, are also optionally advantageous. Preferred wax components are the esters of saturated, monohydric C20 to C60 alcohols and saturated C8 to C30 monocarboxylic acids, preferably in particular a C20 to C40 alkyl stearate, which is available from Koster Keunen Inc. by the name Kesterwachs® K82H.

Natural, chemically modified and synthetic waxes can be used alone or in combination. The teaching contemplated herein thus also comprises the combined use of multiple waxes. Furthermore, a number of wax mixtures, optionally blended with further additives, is commercially available. Examples of mixtures that can be used include those by the designations "Spezialwachs 7686 OE" (mixture of cetyl palmitate, beeswax, microcrystalline wax and polyethylene having a melting point of 73 to 75° C.; manufacturer: Kahl & Co), Polywax® GP 200 (a mixture of stearyl alcohol and polyethylene glycol stearate having a melting point of 47 to 51° C.; manufacturer: Croda) and "Weichceresin® FL 400" (a paraffin jelly/liquid paraffin/wax mixture having a melting point of 50 to 54° C.; manufacturer: Parafluid Mineraldgesellschaft).

The wax (a) is preferably selected from carnauba wax (INCI: Copernicia Cerifera Cera), Myrica Cerifera Fruit Wax (INCI), Rhus Verniciflua Peel Cera (INCI), beeswax (INCI: Beeswax), Petrolatum (INCI), microcrystalline wax, and in particular mixtures thereof.

The wax (a) is particularly preferably a mixture of a plant-based wax, in particular carnauba wax (INCI: Copernicia Cerifera Cera), beeswax (INCI: Beeswax) and Petrolatum (INCI).

The wax or the wax components should be solid at about 25° C. and should melt around >about 37° C.

The agent comprises at least one emulsifier as the further essential component (b). In principle, anionic, cationic, non-ionic and ampholytic surface-active compounds which are suitable for use on the human body can be used as emulsifiers. The ampholytic surface-active compounds comprise zwitterionic surface-active compounds and ampholytes. Non-ionic emulsifiers are preferred.

Non-ionic emulsifiers that can be used include in particular addition products of ethylene oxide to linear fatty alcohols, to fatty acids, to fatty acid alkanolamides, to fatty acid monoglycerides, to sorbitan fatty acid monoesters, to fatty acid glycerides, to methyl glucoside monofatty acid esters, to polydimethyl siloxanes, and mixtures thereof.

The at least one emulsifier (b) is preferably selected from non-ionic emulsifiers such as addition products of about 2 to about 50 moles ethylene oxide to linear fatty alcohols having 8 to 30, preferably 12 to 18 carbon atoms, addition products of about 2 to about 50 moles ethylene oxide and about 1 to about 5 moles propylene oxide to linear fatty alcohols having 8 to 30, preferably 12 to 18 carbon atoms, addition products of about 2 to about 100 moles ethylene oxide to linear fatty acids having 12 to 18 carbon atoms, and mixtures thereof.

Examples of preferred emulsifiers (b) are compounds having the INCI names Steareth-2, Steareth-21, Oleth-10, PEG-100 Stearate or PPG-5-Ceteth-20, and in particular combinations thereof.

Likewise preferred emulsifiers (b) are the esters of fatty acids having 12 to 22 carbon atoms with saccharides. In particular the monoesters and/or diesters of sucrose with stearic acid and/or palmitic acids are preferably used. Examples of particularly preferred emulsifiers are compounds having the INCI names Sucrose Stearate, Sucrose Distearate, or mixtures thereof.

Further preferred emulsifiers (b) are linear fatty acids having 12 to 22 carbon atoms and mixtures thereof. The linear fatty acids can be present in neutralized and/or non-neutralized form, depending on the pH value. Preferably, non-neutralized palmitic acid and/or stearic acid are used as emulsifiers (b).

Likewise preferred emulsifiers (b) are addition products of about 2 to about 20 moles ethylene oxide to beeswax, such as in particular the compounds having the INCI names PEG-6 Beeswax, PEG-8 Beeswax, PEG-12 Beeswax or PEG-20 Beeswax. PEG-8 Beeswax is particularly preferred from this class of emulsifiers.

Another class of emulsifiers (b) that can preferably be used is the monoesters of fatty acids having 12 to 22 carbon atoms with glycerol. In particular the monoesters of glycerol with stearic acid and/or palmitic acids are preferably used. Examples of particularly preferred emulsifiers are compounds having the INCI names Glyceryl Stearate, Glyceryl Palmitate, or mixtures thereof.

In an exceptionally preferred embodiment, the emulsifier (b) is selected from the group consisting of linear fatty acids having 12 to 22 carbon atoms, monoesters of fatty acids having 12 to 22 carbon atoms with glycerol, addition products of about 2 to about 20 moles ethylene oxide to beeswax, and mixtures thereof.

The cosmetic agent comprises the at least one emulsifier in a total amount of about 0.5 to about 20 wt. %, preferably about 2 to about 25 wt. %, and more preferably about 2.5 to about 20 wt. %, based on the total weight of the cosmetic agent.

The cosmetic agent furthermore comprises a cellulose ether as the essential component (c). The amount of cellulose ether, based on the total amount of cosmetic agent, is about 0.01 to about 3 wt. %.

It is preferred that the cellulose ether is selected from the group consisting of methyl cellulose, ethyl cellulose, propyl cellulose, methylethyl cellulose, carboxymethyl cellulose, ethyl carboxymethyl cellulose, hydroxyethyl cellulose, hydroxypropyl cellulose, carboxymethyl hydroxyethyl cellulose, methyl hydroxyethyl cellulose, hydroxypropyl methyl cellulose, ethyl hydroxyethyl cellulose, methyl ethyl hydroxyethyl cellulose, and mixtures thereof. Cellulose ethers that are preferably used are hydroxyethyl cellulose and hydroxypropyl cellulose. In a preferred embodiment, the cellulose ether comprises hydroxyethyl cellulose. In a particularly preferred embodiment, the cellulose ether is hydroxyethyl cellulose.

Preferred cosmetic agents, based on the weight thereof, comprise the cellulose ether or ethers in a total amount of about 0.025 to about 2 wt. %, and more preferably in a total amount of about 0.05 to about 1 wt. %.

The cosmetic agent furthermore comprises propionic acid and/or salt(s) of propionic acid as the essential component (d). Preferably one or more propionic acid salts are used, wherein the use within certain narrow quantity ranges is particularly effective.

For this purpose, among other things the alkali metal salts sodium propionate, potassium propionate, as well as ammonium propionate, magnesium propionate, calcium propionate, zinc propionate, iron propionate and manganese propionate have proven to be particularly suitable. Preferred cosmetic agents comprise salt(s) from the group consisting of sodium propionate, potassium propionate, as well as ammonium propionate, magnesium propionate, calcium propionate, zinc propionate, iron propionate and manganese propionate in a total amount of about 0.01 to about 2 wt. %, preferably about 0.1 to about 1.75 wt. %, and in particular about 0.5 to about 1.5 wt. %, in each case based on the weight of the agent. Particularly preferred salts of propionic acid are selected from sodium propionate, potassium propionate, calcium propionate and mixtures thereof.

Particularly preferred cosmetic agents, based on the weight thereof, comprise about 0.01 to about 2 wt. %, preferably about 0.1 to about 1.75 wt. %, and in particular about 0.5 to about 1.5 wt. % calcium propionate. It may be preferred that component (d) is calcium propionate.

The cosmetic agent comprises water. Preferred cosmetic agents comprise water as the cosmetic carrier. In these embodiments, the cosmetic agent comprises water as the main component. The water content of the cosmetic agents is about 5 to about 90 wt. %, preferably about 15 to about 80 wt. %, and more preferably about 40 to about 75 wt. %, based on the total weight of the cosmetic agent.

The cosmetic agent can furthermore comprise at least one film-forming polymer that is different from the wax component (a). Examples are cationic, anionic, non-ionic or amphoteric polymers. The cosmetic agent can comprise the at least one film-forming polymer (f) in a total amount of about 1 to about 60 wt. %, preferably about 2 to about 50 wt. %, and more preferably about 5 to about 40 wt. %, based on the total weight of the cosmetic agent.

Examples include acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, Bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, poly-beta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA Copolymer, VP/vinyl caprolactam/DMAPA acrylates copolymer, yeast palmitate or styrene/VP copolymer.

Furthermore, siloxanes are suitable as film-forming polymers. These siloxanes can either be water-soluble or water-insoluble. Both volatile and non-volatile siloxanes are suitable, wherein non-volatile siloxanes shall be understood to mean those compounds having a boiling point above about 200° C. at normal pressure. Preferred siloxanes are polydialkylsiloxanes, such as polydimethylsiloxane, polyalkylarylsiloxanes, such as polyphenylmethylsiloxane, ethoxylated polydialkylsiloxanes, and polydialkylsiloxanes containing amine and/or hydroxy groups. Glycosidically substituted silicones may also be used.

Homopolyacrylic acid (INCI: Carbomer), which is commercially available in different embodiments under the name Carbopol®, is also a suitable film-forming polymer.

The film-forming polymer is preferably selected from vinylpyrrolidone-containing polymers. The film-forming polymer is particularly preferably selected from the group consisting of polyvinylpyrrolidone, vinylpyrrolidone/vinyl acetate copolymer, Vinyl Caprolactam/VP/Dimethylaminoethyl Methacrylate Copolymer (INCI), VP/DMAPA Acrylates Copolymer (INCI) and mixtures thereof.

A film-forming polymer that is likewise preferred is the Octylacrylamide/Acrylates/Butylaminoethyl Methacrylate Copolymer (INCI), which is sold by AkzoNobel under the designation "Amphomer®."

In particular nourishing components, such as oils, should be mentioned as further suitable auxiliary agents and additives.

Suitable oils are selected from among the esters of the linear or branched, saturated or unsaturated fatty alcohols having 2 to 30 carbon atoms with linear or branched, saturated or unsaturated fatty acids having 2 to 30 carbon atoms, which may be hydroxylated. These include cetyl-2-ethylhexanoate, 2-hexyldecyl stearate (for example, Eutanol® G 16 S), 2-hexyldecyl laurate, isodecyl neopentanoate, isononyl isononanoate, 2-ethylhexyl palmitate (for example, Cegesoft® C 24) and 2-ethylhexyl stearate (for example Cetiol® 868). Likewise preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate. Cetyl-2-ethylhexanoate is particularly preferred.

Further preferred oils are selected from natural and synthetic hydrocarbons, particularly preferably from mineral oils, paraffin oils, $C_{18}$ to $C_{30}$ isoparaffins, in particular isoeicosane, polyisobutene and polydecene, which are available under the designation Emery® 3004, 3006, 3010 or under the designation Ethylflo® from Albemarle or Nexbase® 2004G from Nestle, for example, and further selected from $C_8$ to $C_{16}$ isoparaffins, in particular from isodecane, isododecane, isotetradeane and isohexadecane, and mixtures thereof, as well as 1,3-bis(2-ethylhexyl)cyclohexane (available under the trade name Cetiol® S from BASF, for example).

Further preferred oils are selected from the benzoic acid esters of linear or branched C8-22 alkanols. Particularly preferred are benzoic acid-C12-C15-alkyl esters, for example available as the commercial product Finsolv® TN, benzoic acid isostearyl esters, for example available as the commercial product Finsolv® SB, ethylhexyl benzoate, for example available as the commercial product Finsolv® EB, and benzoic acid octyldodecyl esters, for example available as the commercial product Finsolv® BOD.

Further preferred oils are selected from fatty alcohols having 6 to 30 carbon atoms, which are unsaturated, or branched and saturated, or branched and unsaturated. The branched alcohols are frequently also referred to as Guerbet alcohols since they can be obtained by way of the Guerbet reaction. Preferred alcohol oils are 2-hexyldecanol (Eutanol® G 16), 2-octyldodecanol (Eutanol® G), 2-ethylhexyl alcohol and isostearyl alcohol.

Further preferred oils are selected from mixtures of Guerbet alcohols and Guerbet alcohol esters, for example the commercial product Cetiol® PGL (2-hexyldecanol and 2-hexyldecyl laurate).

Further preferred cosmetic oils are selected from the triglycerides (=triple esters of glycerol) of linear or branched, saturated or unsaturated, optionally hydroxylated C8-30 fatty acids. The use of natural oils can be particularly preferred, such as amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, currant seed oil, jojoba oil, linseed oil, macadamia nut oil, corn oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn kernel oil, sesame oil, soy bean oil, sunflower oil, grape seed oil, walnut oil, wild rose oil, wheat germ oil, and the liquid components of coconut oil, and the like. However, synthetic triglyceride oils, in particular capric/caprylic triglycerides, such as the commercial products Myritol® 318, Myritol® 331 (BASF) or Miglyol® 812 (Hüls) comprising unbranched fatty acid esters and glyceryl triisostearol with branched fatty acid esters are also preferred.

Further preferred cosmetic oils are selected from the dicarboxylic acid esters of linear or branched C2 to C10 alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further preferred cosmetics oils are selected from the addition products of 1 to 5 propylene oxide units to monohydric or polyhydric C8-22 alkanols, such as octanol, decanol, decanediol, lauryl alcohol, myristyl alcohol, and stearyl alcohol, for example PPG-2 myristyl ether and PPG-3 myristyl ether (Witconol® APM).

Further preferred cosmetic oils are selected from the addition products of at least 6 ethylene oxide units and/or propylene oxide units to monohydric or polyhydric C3-22 alkanols, such as glycerol, butanol, butanediol, myristyl alcohol and stearyl alcohol, which may optionally be esterified, such as PPG-14 butyl ether (Ucon Fluid® AP), PPG-9 butyl ether (Breox® B25), PPG-10 butanediol (Macol® 57), PPG-15 stearyl ether (Arlamol® E), and glycereth-7-di-isononanoate.

Further preferred cosmetic oils are selected from the C8 to C22 fatty alcohol esters of monovalent or polyvalent C2 to C7 hydroxycarboxylic acids, in particular the esters of glycolic acid, lactic acid, malic acid, tartaric acid, citric acid, and salicylic acid. Such esters based on linear C14/15 alkanols, such as C12 to C15 alkyl lactate, and of C12/13 alkanols branched at the 2-position, may be purchased under the trademark Cosmacol® from Nordmann, Rassmann GmbH & Co., Hamburg, in particular the commercial products Cosmacol® ESI, Cosmacol® EMI, and Cosmacol® ETI.

Further preferred cosmetic oils are selected from the symmetric, asymmetric or cyclic esters of carbonic acid with $C_{3-22}$ alkanols, $C_{3-22}$ alkane diols or $C_{3-22}$ alkane triols, such as dicaprylyl carbonate (Cetiol® CC), or the esters according to the teaching of DE 19756454 A1, and in particular glycerol carbonate.

Further cosmetic oils that may be preferred are selected from the esters of dimers of unsaturated $C_{12}$ to $C_{22}$ fatty acids (dimer fatty acids) comprising monohydric linear, branched or cyclic $C_2$ to $C_{18}$ alkanols or polyhydric linear or branched $C_2$ to $C_6$ alkanols.

Further cosmetic oils that are suitable are selected from silicone oils, which include, for example, dialkyl and alkyaryl siloxanes, such as cyclopentasiloxane, cyclohexasiloxane, dimethylpolysiloxane and methylphenylpolysiloxane, but also hexamethyldisiloxane, octamethyltrisiloxane and decamethyltetrasiloxane. Volatile silicone oils, which may be cyclic, can be preferred, such as octamethylcyclotetrasiloxane, decamethylcyclopentasiloxane and dodecamethylcyclohexasiloxane, and mixtures thereof, as they can be found in the commercial products DC 244, 245, 344 and 345 from Dow Corning, for example. Volatile linear silicone oils are likewise suitable, in particular hexamethyldisiloxane ($L_2$), octamethyltrisiloxane ($L_3$), decamethyltetrasiloxane ($L_4$), and arbitrary mixtures of two and three of $L_2$, $L_3$ and/or $L_4$, preferably mixtures such as those present, for example, in the commercial products DC 2-1184, Dow Corning® 200 (0.65 cSt) and Dow Corning® 200 (1.5 cSt) from Dow Corning. Preferred non-volatile silicone oils are selected from higher molecular weight linear dimethylpolysiloxanes, commercially available, for example, under the designation Dow Corning® 190, Dow Corning® 200 Fluid having kinematic viscosities (25° C.) in the range of 5 to 100 cSt, preferably 5 to 50 cSt, or 5 to 10 cSt, and dimethylpolysiloxane having a kinematic viscosity (25° C.) of approximately 350 cSt.

It may be exceptionally preferred to use mixtures of the aforementioned oils.

The agent can also include at least one protein hydrolysate and/or one of the derivatives thereof, for example, as a nourishing component. Protein hydrolysates are product mixtures that are obtained by the acidically, basically or enzymatically catalyzed degradation of proteins. The term "protein hydrolysates" shall also be understood to cover total hydrolysates and individual amino acids and the derivatives thereof, as well as mixtures of different amino acids. The molecular weight of the protein hydrolysates that can be used ranges between about 75, the molecular weight for glycine, and about 200,000; the molecular weight is preferably about 75 to about 50,000, and especially particularly preferably about 75 to about 20,000 daltons.

The agent can furthermore include at least one vitamin, a provitamin, a vitamin precursor and/or one of the derivatives thereof as a nourishing component. Vitamins, provitamins and vitamin precursors that are usually assigned to the groups A, B, C, E, F and H are preferred.

To set the pH, the cosmetic agent can furthermore comprise neutralizers or pH setting agents. Examples of neutralizers that are used in cosmetic agents are primary amino alcohols such as Aminomethyl Propanol (INCI), which is commercially available under the designation AMP-ULTRA® PC, for example, such as AMP-ULTRA® PC 2000.

The agents can furthermore comprise additional cosmetically acceptable preservatives. One example of a preservative that can preferably be used is 2-phenoxyethanol.

The cosmetic agent contemplated herein can be formulated in the forms customary for the temporary shaping of hair, for example as a wax, paste, lotion or clay. The cosmetic agents are preferably offered in jars or crucibles.

An exemplary embodiment also relates to the cosmetic, non-therapeutic use of cosmetic agents contemplated herein for temporarily shaping keratin fibers, and in particular human hair, and to a method for temporarily reshaping keratin fibers, and in particular human hair, in which the cosmetic agent is applied to keratin fibers.

An exemplary embodiment also relates to the use of propionic acid and/or salts of propionic acid in a cosmetic agent for temporarily reshaping keratin fibers, and in particular human hair, which is preferably present in the form of an emulsion, for increasing the physical stability of the cosmetic agent. Preferably, cosmetic agents contemplated herein are used.

Tabular Overview

The composition of several preferred cosmetic agents can be derived from the following tables (information as solids content and in percent by weight based on the total weight of the cosmetic agent, unless indicated otherwise).

|  | Formula 1 | Formula 2 | Formula 3 |
|---|---|---|---|
| (a) Wax | 1-30 | 2-25 | 2.5-20 |
| (b) Emulsifier | 0.5-20 | 0.75-17.5 | 1-15 |
| (c) Cellulose ether | 0.01-3 | 0.0225-2 | 0.05-1 |
| (d) Propionic acid and/or salt(s) of propionic acid | 0.01-2 | 0.1-1.75 | 0.5-1.5 |
| (e) Water | 5-90 | 15-80 | 40-75 |
| Misc. | to make up to 100 | to make up to 100 | to make up to 100 |

|  | Formula 1a | Formula 2a | Formula 3a |
|---|---|---|---|
| (a) Wax | 1-30 | 2-25 | 2.5-20 |
| (b) Emulsifier | 0.5-20 | 0.75-17.5 | 1-15 |
| (c) Cellulose ether | 0.01-3 | 0.0225-2 | 0.05-1 |
| (d) Propionic acid and/or salt(s) of propionic acid | 0.01-2 | 0.1-1.75 | 0.5-1.5 |
| (e) Water | 5-90 | 15-80 | 40-75 |
| (f) Film-forming polymer | 1-60 | 2-50 | 5-40 |
| Misc. | to make up to 100 | to make up to 100 | to make up to 100 |

|  | Formula 1b | Formula 2b | Formula 3b |
|---|---|---|---|
| (a) Plant-based wax and/or beeswax and/or petrolatum | 1-30 | 2-25 | 2.5-20 |
| (b) Emulsifier | 0.5-20 | 0.75-17.5 | 1-15 |
| (c) Hydroxyethyl cellulose | 0.01-3 | 0.0225-2 | 0.05-1 |
| (d) Salt(s) of propionic acid | 0.01-2 | 0.1-1.75 | 0.5-1.5 |
| (e) Water | 5-90 | 15-80 | 40-75 |
| (f) Non-ionic and/or amphoteric film-forming polymer | 0 or 1-60 | 0 or 2-50 | 0 or 5-40 |
| Misc. | to make up to 100 | to make up to 100 | to make up to 100 |

|  | Formula 1c | Formula 2c | Formula 3c |
|---|---|---|---|
| (a) Plant-based wax and/or beeswax and/or petrolatum | 1-30 | 2-25 | 2.5-20 |
| (b) Non-ionic emulsifier | 0.5-20 | 0.75-17.5 | 1-15 |
| (c) Hydroxyethyl cellulose | 0.01-3 | 0.0225-2 | 0.05-1 |
| (d) Salt(s) of propionic acid | 0.01-2 | 0.1-1.75 | 0.5-1.5 |
| (e) Water | 5-90 | 15-80 | 40-75 |
| (f) Vinylpyrrolidone-containing polymer and/or Octylacrylamide/Acrylates/Butylaminoethyl Methacrylate Copolymer (INCI) | 0 or 1-60 | 0 or 2-50 | 0 or 5-40 |
| Misc. | to make up to 100 | to make up to 100 | to make up to 100 |

|  | Formula 1d | Formula 2d | Formula 3d |
|---|---|---|---|
| (a) Plant-based wax and/or beeswax and/or petrolatum | 1-30 | 2-25 | 2.5-20 |
| (b) Linear fatty acids having 12 to 22 carbon atoms and/or monoesters of fatty acids having 12 to 22 carbon atoms with glycerol and/or addition products of 2 to 20 moles ethylene oxide to beeswax | 0.5-20 | 0.75-17.5 | 1-15 |
| (d) Hydroxyethyl cellulose | 0.01-3 | 0.0225-2 | 0.05-1 |
| (e) Ca salt of propionic acid | 0.01-2 | 0.1-1.75 | 0.5-1.5 |
| (e) Water | 5-90 | 15-80 | 40-75 |
| (f) Vinylpyrrolidone-containing polymer and/or Octylacrylamide/Acrylates/Butylaminoethyl Methacrylate Copolymer (INCI) | 0 or 1-60 | 0 or 2-50 | 0 or 5-40 |
| Misc. | to make up to 100 | to make up to 100 | to make up to 100 |

"Misc" shall be understood to mean further customary components of cosmetic agents for temporarily shaping keratin fibers, such as perfumes/aromatic substances, pH-setting agents and/or nourishing components.

EXAMPLES

The following cosmetic agents were produced:

| Component/raw material | INCI name | Example 1 (% by weight) |
|---|---|---|
| Carnauba wax | *Copernicia Cerifera* Cera | 7.5 |
| Beeswax | Beeswax | 7.5 |
| Petrolatum | Petrolatum | 4 |
| Hydroxyethyl cellulose | Hydroxyethylcellulose | 0.1 |
| Calcium propionate | Calcium Propionate | 1 |
| Glyceryl monostearate | Glyceryl Stearate | 5 |
| Ethoxylated beeswax (8EO) | PEG-8 Beeswax | 1 |
| Palmitic acid | Palmitic Acid | 1 |
| Stearic acid | Stearic Acid | 1 |
| Isopropyl myristate | Isopropyl Myristate | 5.6 |
| 2-amino-2-methylpropanol | Aminomethyl Propanol | 0.25 |
| Dyes |  | 0.077 |
| 2-Phenoxyethanol | Phenoxyethanol | 0.8 |
| Perfume | Perfume (Fragrance) | 1.7 |
| Water | Aqua (Water) | to make 100 |

The quantity information in the tables is provided in % by weight of the respective raw material, based on the total agent.

The cosmetic agent 1 was physically and microbiologically stable over a period of 12 weeks at various temperatures (room temperature, 0° C., 45° C., −10° C.).

All produced cosmetic agents exhibited outstanding application and distribution properties in the hair and showed no residue on the treated hair.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A cosmetic agent for temporarily shaping keratin fibers, comprising:
   (a) at least one wax having a melting point above about 37° C. in a total amount of about 2.5 to about 20 wt. %, wherein the at least one wax comprises a mixture of a plant-based wax, Petrolatum (INCI), and beeswax (INCI: Beeswax);
   (b) at least one emulsifier in a total amount of about to about 15 wt. %, wherein the at least one emulsifier comprises a mixture of linear fatty acids having 12 to 22 carbon atoms, monoesters of fatty acids having 12 to 22 carbon atoms with glycerol, and addition products of about 2 to about 20 moles ethylene oxide to beeswax;
   (c) at least one cellulose ether in a total amount of about 0.05 to about 1 wt. %, wherein the at least one cellulose ether comprises hydroxyethyl cellulose;

(d) propionic acid and/or salts of propionic acid in a total amount of about 0.5 to about 1.5 wt. %, wherein the propionic acid and/or salts of propionic acid comprise calcium propionate; and (e) water in a total amount of about 40 to about 75 wt. %, wherein the weight percent is based in each case on the total weight of the cosmetic agent.

2. The cosmetic agent according to claim 1, further comprising at least one cosmetic oil.

3. The cosmetic agent according to claim 1, wherein the cosmetic agent has the form of a hair wax, paste, lotion or clay.

4. The cosmetic agent according to claim 1, further comprising at least one film forming polymer in a total amount of about 5 to about 40 wt. %.

5. A method for temporarily shaping keratin fibers, the method comprising the steps of:

providing a cosmetic agent comprising:

(a) at least one wax having a melting point above about 37° C. in a total amount of about 2.5 to about 20 wt. %, wherein the at least one wax comprises a mixture of a plant-based wax, Petrolatum (INCI), and beeswax (INCI: Beeswax);

(b) at least one emulsifier in a total amount of about to about 15 wt. %, wherein the at least one emulsifier comprises a mixture of linear fatty acids having 12 to 22 carbon atoms, monoesters of fatty acids having 12 to 22 carbon atoms with glycerol, and addition products of about 2 to about 20 moles ethylene oxide to beeswax;

(c) at least one cellulose ether in a total amount of about 0.05 to about 1 wt. %, wherein the at least one cellulose ether comprises hydroxyethyl cellulose;

(d) propionic acid and/or salts of propionic acid in a total amount of about 0.5 to about 1.5 wt. %, wherein the propionic acid and/or salts of propionic acid comprise calcium propionate; and (e) water in a total amount of about 40 to about 75 wt. %, wherein the weight percent is based in each case on the total weight of the cosmetic agent, and applying the cosmetic agent to the keratin fibers.

6. The method according to claim 5, wherein the cosmetic agent is provided in the form of a hair wax, paste, lotion or clay.

7. The method according to claim 5, wherein the cosmetic agent further comprises at least one cosmetic oil.

8. The method according to claim 5, wherein the cosmetic agent further comprises at least one film forming polymer in a total amount of about 5 to about 40 wt. %.

* * * * *